United States Patent [19]

Johnson, Jr. et al.

[11] Patent Number: 5,578,085

[45] Date of Patent: Nov. 26, 1996

[54] BALLOON PROSTHESIS FOR THE LUNG AND METHODS OF MAKING AND USING SAME

[75] Inventors: Robert L. Johnson, Jr.; Connie C. W. Hsia, both of Dallas, Tex.

[73] Assignee: Board of Regents The University of Texas System, Austin, Tex.

[21] Appl. No.: 206,532

[22] Filed: Mar. 4, 1994

Related U.S. Application Data

[63] Continuation-in-part of Ser. No. 109,695, Aug. 19, 1993, abandoned, which is a continuation of Ser. No. 800,509, Nov. 27, 1991, abandoned.

[51] Int. Cl.$^6$ .................................................... A61F 2/02
[52] U.S. Cl. .................... 623/11; 623/8; 623/12; 623/66; 606/192; 606/195
[58] Field of Search ................... 623/7, 8, 11, 12, 623/66; 604/27–28, 36–38, 41, 45; 606/191, 192, 195; 434/262, 267, 265

[56] References Cited

U.S. PATENT DOCUMENTS

| | | | |
|---|---|---|---|
| 3,570,494 | 3/1971 | Gottschalk | 606/196 |
| 4,095,295 | 6/1978 | Lake | 623/8 |
| 4,643,733 | 2/1987 | Becker . | |
| 4,651,717 | 3/1987 | Jakubczak | 623/8 |
| 4,666,447 | 5/1987 | Smith et al. | 623/8 |
| 4,685,446 | 8/1987 | Choy . | |
| 4,773,865 | 9/1988 | Baldwin | 434/267 |
| 4,800,901 | 1/1989 | Rosenberg . | |
| 4,841,992 | 6/1989 | Sasaki et al. | 623/8 |
| 4,969,898 | 11/1990 | Calogero | 623/8 |
| 4,969,899 | 11/1990 | Cox . | |
| 5,146,933 | 9/1992 | Boyd | 623/11 |

OTHER PUBLICATIONS

D. Rasch et al., "Right Pneumonectomy Syndrome in Infancy Treated with an Expandable Prosthesis," 50 *Ann. Thorac. Surg.*, 127–29 (1990).

K. Wasserman et al., "Post–Pneumonectomy Syndrome: Surgical Correction Using Silastic Implants," 75 *Chest* 1 (Jan. 1979).

R. Powell, et al., "Pneumonectomy in Infants and Children: The Use of a Prosthesis to Prevent Mediastinal Shift and Its Complications," 14 *J. Pediatric Surg.* 231 (Jun. 1979).

Reference BD, J. Johnson, et al., "The Clinical Use of a Prosthesis to Prevent Overdistention of the Remaining Lung Following Pneumonectomy," 18 *J. Thorac. Surg.* 164 (1949).

*Primary Examiner*—Mary Beth Jones
*Assistant Examiner*—P. Zuttarelli

[57] ABSTRACT

A prosthesis is provided to replace an excised lung, comprising a hollow balloon-like structure formed generally in the shape of the lung, a filling tube, and a filling port. This prosthesis occupies the chest cavity left vacant after pneumonectomy to inhibit mediastinal shifting and overdistension and displacement of the remaining lung and other organs. This prosthesis also compliantly supports the heart and prevents the heart from contacting and adhering to other structures in the chest cavity. The volume of the prosthesis can be adjusted subsequent to implantation without subsequent surgery through a subcutaneous septal port. A combination of gases is selected to fill the prosthesis to minimize the volume change due to transfer of gas across the balloon membrane. Also provided are a method for preventing mediastinal shift and overdistension and displacement of organs following pneumonectomy using the prosthesis of this invention, and a method of making the prosthesis.

25 Claims, 10 Drawing Sheets

BALLOON PROSTHESIS FOR THE LUNG AND METHODS OF MAKING AND USING SAME

The United States Government may have certain rights in the present invention pursuant to Grant No. HL 40070 awarded by the National Institutes of Health.

This application is a continuation-in-part of application Ser. No. 08/109,695, filed Aug. 19, 1993, now abandoned which is a continuation of prior application Ser. No. 07/800, 509 filed on Nov. 27, 1991, now abandoned.

BACKGROUND OF THE INVENTION

1. Field of the Invention

This invention relates to prosthetic appliances for humans and other animals, and in particular it relates to a prosthetic device to occupy the chest cavity left vacant after excision of a lung. The prosthesis of this invention performs the separating and supporting functions performed by the lung, without interfering with the performance of the heart or any other organs and without impairing the breathing function of the remaining lung. This invention also relates to a method for making and using such a prosthesis.

2. Description of Related Art

The removal of one lung (i.e. pneumonectomy) is a surgical procedure not uncommonly performed for treatment of cancer, trauma, or infection of the lung. Prevention of overdistension of the remaining lung after pneumonectomy has been a concern to thoracic surgeons for many years. They anticipated that overdistension would cause distortions of remaining structures inside the thorax leading to abnormal heart and lung function. Many surgical procedures were designed to prevent overexpansion. In the 1940's investigators placed hollow lucite balls in the vacant chest cavities of dogs and humans to prevent overdistension of the remaining lung and to maintain the mediastinum in the midline following pneumonectomy. This work was described in Johnson et al., *Journal of Thoracic Surgery* 18:164 (1949).

Other substances and devices have been used to replace an excised lung and to correct the problems associated therewith, including gelatin foam, plastic sponge (Ivalon) and a polythene bag filled with fiberglass. Since the early 1960's these procedures have generally been abandoned as unnecessary.

More recently, it was noted that in several very young patients respiratory difficulties occurred after pneumonectomy due to tracheal kinking and deformity from marked mediastinal shift following pneumonectomy. A degree of success was reported by physicians who implanted silicone testicular and. breast prostheses in the thoracic cavities of infants and young children to avoid and cure such difficulties, as was reported in Powell et al., *Journal of Pediatric Surgery* 14:231 (1979).

Success in correcting tracheal shift and overdistension of the remaining lung following pneumonectomy was also reported after implantation of silicone implants (similar to breast implants) in a 25 year old man in 1975, as was reported in Wasserman et al., *Chest* 75:78 (1979).

Use of an expandable prosthesis to remedy problems associated with a removed lung was reported in Rasch et al., *Annals of Thoracic Surgery* 15:127 (1990). The reference indicated that an inflatable tissue expander with a subcutaneous injection port was implanted in a 5 month old infant. A 125-mL Surgitek inflatable tissue expander was inserted into the right pleural space and inflated with 60-mL of saline solution, which effectively returned the heart and mediastinal structures to near their natural positions. Five months after the operation the patient's respiratory difficulty returned and was relieved by injecting an additional 30-mL of saline solution into the prosthesis.

Numerous types of tissue expanders have been used by medical practitioners for non-thoracic purposes, such as those disclosed in, for example, U.S. Pat. Nos. 4,095,295, 4,643,733, 4,800,901, 4,685,446, and 4,969,899. These are all designed for use in muscular and cutaneous tissue and are filled with a fluid or gelatinous material. Ordinary tissue expanders are not well suited for use as lung prostheses, however, because (a) they do not conform to the shape of the lung, so normal anatomy is not restored, (b) they generally contain saline, which is heavy and which does not restore normal compliance around the heart, and (c) they are not expandable to the extent required to permit implantation in a child and subsequent expansion to accommodate normal growth. A normal lung comprises three major exterior surfaces. The "rib cage surface" is convex and is adjacent to and conforms to the configuration of the inner surface of the rib cage. The lower "diaphragmatic surface" is concave and is adjacent to and conforms to the configuration of the thoracic surface of the corresponding hemi-diaphragm. The "cardiac and mediastinal surface" is generally concave and irregularly shaped to conform to the contours of the heart and large mediastinal vessels such as the aorta and the pulmonary arteries. The contour of this surface varies significantly from patient to patient because there are considerable variations in the normal shape and size of the heart. The right lung normally comprises 3 lobes (upper, middle and lower) and the left lung normally comprises 2 lobes (upper and lower) separated by fissures. In response to injury or disease, an entire lung or one or more lobes of a lung may be resected.

Other space-filling artificial organs have constructed, for example the artificial bladder disclosed in U.S. Pat. No. 4,044,401 is intended to occupy a space normally occupied by a bladder. Such a device is preferably rigid and made of hard plastic, making it unsuitable for use in a dynamic and structurally constrained location, such as the thoracic cavity. Furthermore, such devices are not designed to be filled with inert gasses or other materials, allowing proper fit and expandability following growth of the patient It has also been long known that the work tolerance of a human is significantly lowered following pneumonectomy, and it was assumed that the reduced tolerance was due to lowered respiratory capacity. The inventors and others have recently determined that the remaining lung is often adequate to supply the body's oxygen mediastinal shift and overdistension and displacement of the remaining organs after pneumonectomy is provided. The lung prosthesis according to this invention is hollow (or fluid-filled) and lightweight, yet it effectively and compliantly supports the heart and mediastinal structures and inhibits their movement from normal positions, preventing. adhesion of the heart to other structures to avoid fibrous encasement of the heart. The prosthesis may be custom molded to fit the chest cavity into which it is intended to be placed and provided with a subcutaneous septal port which allows fluid to be injected into and withdrawn from the implanted prosthesis without additional surgery. An elastic material may be chosen to construct the prosthesis to permit volume changes as the patient grows.

A method is provided for custom molding a prosthesis according to this invention to match the size and shape of the chest cavity of each patient, although it may be feasible to provide a plurality of prostheses across a range of sizes, either individually or in a kit, from which a physician could select a suitable prosthesis. The prosthesis may be designed to allow for uniform expansion of the prosthesis to accommodate growth of a young patient while maintaining its anatomically correct shape over a range of volumes.

The presently preferred custom molding method of making a balloon prosthesis according to this invention comprises obtaining a computer model of the chest cavity the prosthesis is intended to occupy using non-invasive imaging techniques, for example, magnetic resonance imaging or computer tomographic (CT) scanning. A three dimensional physical model may be made based on the computer model, from which a mold may be constructed to form the balloon. The computer model may be generated at the hospital or clinic where the patient is examined and transferred to the balloon fabricator, or it may be generated by the fabricator.

The invention also includes a method for preventing mediastinal shift and overdistension and displacement of organs following pneumonectomy, comprising providing a prosthetic balloon as described herein, implanting it in a patient following needs, and that the reduced ability to work is due to other physiological changes that occur after pneumonectomy. The heart is ordinarily held in place by the cardiac fossa, a compliant cavity formed largely by the shape of the lungs around the heart. When one lung is removed, it has been observed that the heart tends to be pushed against the rigid rib cage and to become attached thereto by relatively non-compliant fibrous tissue. These anatomical changes result in the heart muscle being surrounded by much less compliant structures than is normal, reducing the heart's ability to expand freely and thereby impairing cardiovascular performance.

It is therefore desirable to provide a method of preventing mediastinal shift and overdistension and displacement of the visceral organs following pneumonectomy, and to provide a prosthesis to occupy the space in the chest cavity vacated after pneumonectomy to maintain a compliant cardiac fossa, to prevent the heart from being displaced from its normal position, to inhibit overdistension of the remaining lung, and to maintain the mediastinum near the midline. It is further desirable to provide as light a prosthesis as possible to reduce the work required to support it, while providing a safe and reliable device for long term implantation. Also, it is desirable that a lung prosthesis be adapted to permit adjustment to its volume by injection and withdrawal of fluid (liquid or gas) without additional surgery, and that the prosthesis be expandable to permit its use in a growing patient by periodically injecting additional fluid to increase the volume of the prosthesis. Finally, methods by which such a prosthetic device may be constructed and used are desired. The present invention provides a solution to the long-felt need for a functional prosthesis that overcomes many of the limitations of prior developmental attempts.

SUMMARY OF THE INVENTION

The goals outlined above are in large part achieved by the device and method of the present invention. A method of preventing pneumonectomy, filling the balloon with fluid, and adjusting the volume of the balloon as desired. In a preferred embodiment, the balloon may be implanted at the time of surgery to remove the damaged lung, and the balloon may be filled to occupy the vacant chest cavity without being under tension and without applying pressure to the adjacent organs and structures. Subsequent to surgical implantation, the volume of the balloon may be adjusted without requiring surgery by accessing the subcutaneous septal port of the preferred embodiment with a hypodermic needle and selectively injecting or withdrawing fluid from the prosthesis.

In a preferred embodiment, the prosthesis may be filled with either gas or liquid. In a child where growth is anticipated, a gaseous filler is desirable so the volume inside the prosthesis can be periodically adjusted, and the gas composition may be selected to minimize volume change due to transfer of gas across the wall of the prosthesis. Once growth of the patient is complete and no further change in lung volume is anticipated, the gas may be withdrawn and replaced with a light liquid such as a silicone or saline solution.

The present invention therefore provides an improved prosthesis for occupying the vacant chest cavity after a pneumonectomy. It also provides methods for making the prosthesis and for using the prosthesis to prevent or correct mediastinal shift and overdistension of the remaining lung, and to provide a substitute cardiac fossa to compliantly support the heart. The prosthesis of this invention is lightweight and safe, and it can be adjusted after implantation without surgery as necessary to compensate for growth of the patient or other factors that might alter the shape or volume of the patient's chest. These and other advantages of the present invention will be further appreciated from the drawings and from the detailed description provided below.

BRIEF DESCRIPTION OF THE DRAWINGS

So that the manner in which the herein described advantages and features of the present invention, as well as others which will become apparent, are attained and can be understood in detail, more particular description of the invention summarized above may be had by reference to the embodiment thereof which is illustrated in the appended drawings, which drawings form a part of this specification.

It is to be noted, however, that the appended drawings illustrate only exemplary embodiments of the invention and are therefore not to be considered limiting of its scope, for the invention may admit to other equally effective embodiments.

DESCRIPTION OF THE PREFERRED EMBODIMENTS

Figure 1:
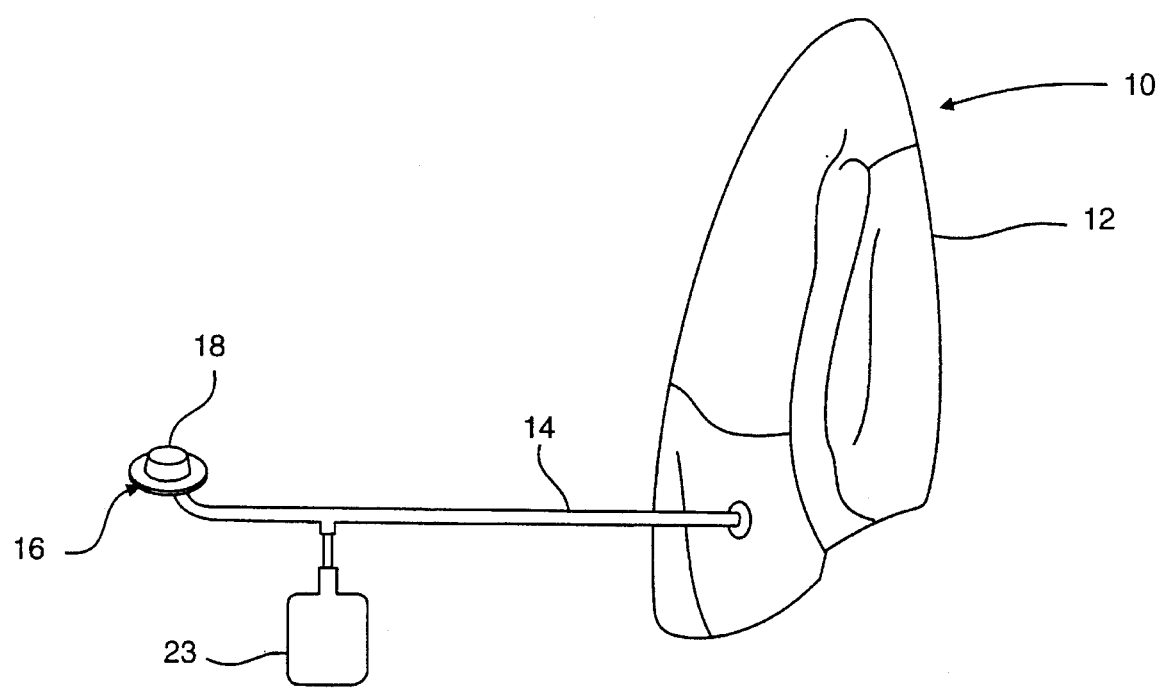
FIG. 1 is a perspective view of a prosthesis manufactured in accordance with this invention.
Figure 2:
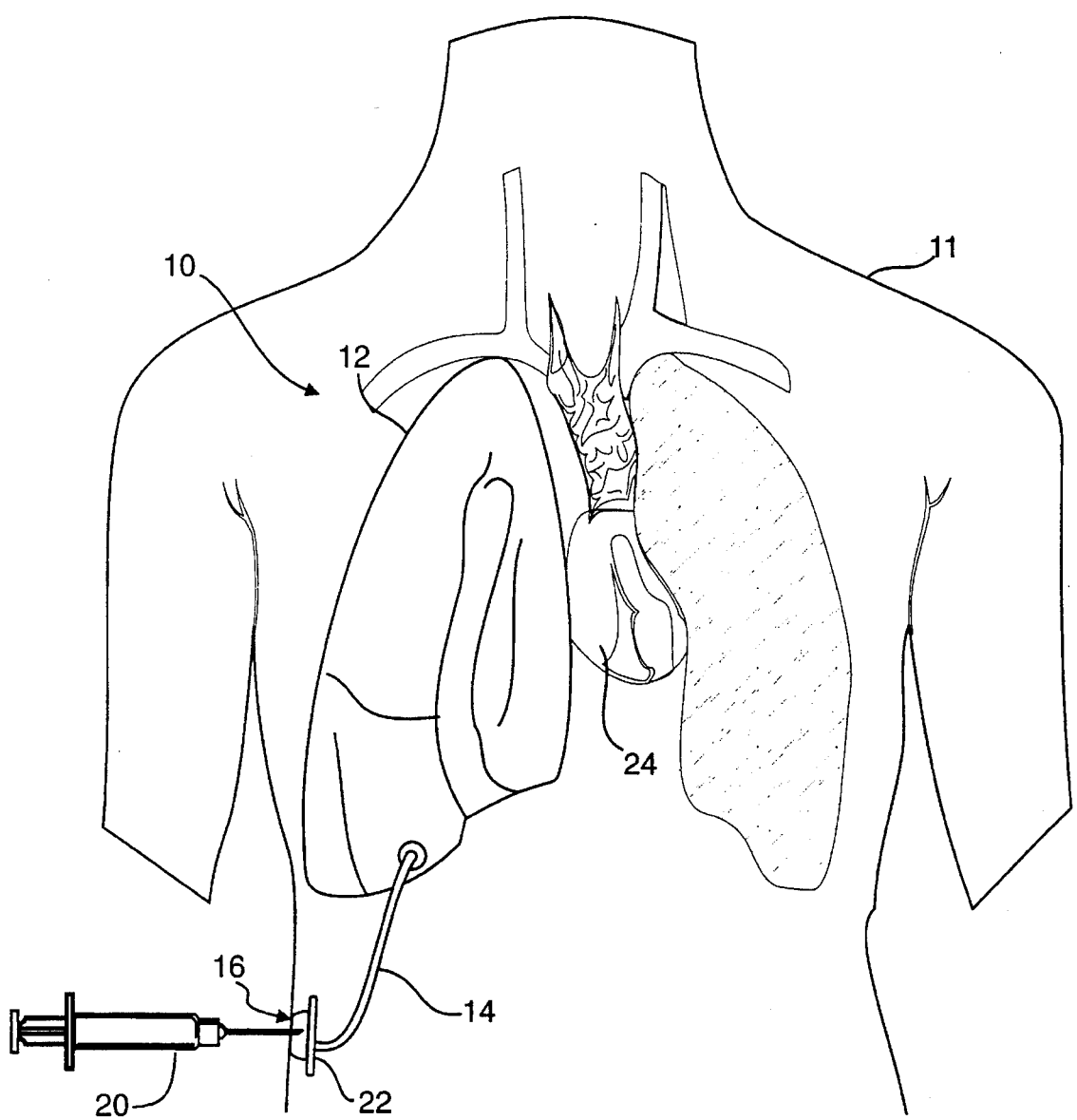
FIG. 2 illustrates the prosthesis of this invention in position in a person's chest, with the subcutaneous septal port located on the lower lateral portion of the patient's torso.

Referring to FIGS. 1 and 2, in a preferred embodiment a hollow balloon-like silicone prosthesis 10 is surgically inserted into the vacant chest cavity of a patient 11 who has undergone pneumonectomy. Balloon 12 of prosthesis 10 may be sized and shaped to occupy the vacant cavity so as to separate and support the walls of the chest cavity and the surrounding organs such as the heart and the remaining lung. At surgery, after one lung or a portion thereof has been removed, balloon 12 may be placed in the vacant chest cavity and filled to a volume necessary to assume the shape and size of the removed lung tissue. The thorax is then closed in layers. Any air surrounding the prosthesis 10 after closure will be resorbed by the patient's body.

The prosthesis 10 may be filled with any suitable fluid, either gaseous or liquid. In a preferred embodiment, the prosthesis is gas filled, either with air or any other suitable gas or combination of gases. It has been noted in experimental use of a balloon prosthesis in a dog that when a similar prosthesis is air-filled it tends to lose volume due to transfer of oxygen molecules out of the balloon across the silicone membrane of the tested prosthesis. In a preferred embodiment, the prosthesis is filled in part with sulfur hexafluoride ($SF_6$), the large molecules of which are unable to permeate the silicone material of the prosthesis. Experiments have also revealed, however, that when the balloon is filled with $SF_6$ it tends to gain volume and pressure due to transfer of $CO_2$ across the silicone membrane into the balloon. In a more preferred embodiment, the prosthesis is filled with a mixture of air and $SF_6$ in a proportion that inhibits the prosthesis from either expanding or contracting due to transfer of gasses across the silicone membrane. Empirical observation indicates that a preferred proportion of air to $SF_6$ is approximately 50% air to 50% $SF_6$. Light liquids such as silicone, as well as gaseous mixtures of air with other inert gases such as neon and krypton, may also be suitable for inflation of the prosthesis.

To enable a physician to monitor and adjust the amount and composition of fluid in the prosthesis, means may be provided for non-surgical access to the interior of the prosthesis after implantation. Referring to FIG. 1, in a preferred embodiment balloon 12 of the prosthesis is provided with a filling tube 14, the interior of which is in communication with the interior of balloon 12. The tube 14 is placed in the patient's body such that its distal end 22 can be accessed by a physician without major surgery. The distal end 22 may be, for example, extended exterior to the patient's body through an infection resistant cutaneous penetration, or it may be terminated subcutaneously. In a preferred embodiment, distal end 22 of tube 14 is connected to a subcutaneous septal port 16. The port is implanted under the patient's skin at an accessible location, and the physician can access the interior of the balloon/tube/port combination by sterilely inserting a hypodermic needle 20 through self-sealing septum 18 of port 16 for injecting and removing gases or other materials from the prosthesis. The septum 18 will typically be self-sealing upon withdrawal of needle 20 therefrom.

It is to be noted that, in a preferred embodiment, prosthesis 10 is not under pressure, and the aforementioned access means is sufficient to prevent fluids from unintentionally entering or escaping the prosthesis 10 through septal port 16. In a preferred embodiment balloon 12 is constructed to be slightly larger than the chest cavity it is intended to occupy so that the balloon membrane is not under tension when filled to the selected volume. For example and without limitation, in a preferred embodiment balloon 12 is constructed approximately 10% larger than the chest cavity it is intended to occupy at the end of a normal exhalation.

In an alternative embodiment, balloon 12 of prosthesis 10 is designed to permit uniform, shape-retaining expansion. This expandable embodiment is intended primarily for implantation in children and youth, and it allows periodic non-surgical expansion of the prosthesis as the patient grows. In this embodiment and in other embodiments, regions of the balloon that are under the most stress or strain during expansion may be made thicker or reinforced with materials such as Dacron. Fluid may be added at a rate commensurate with the rate of growth of the patient's chest cavity. The prosthesis is designed to expand in volume while retaining its overall shape and compliance, so its support function is maintained.

In a preferred embodiment, pressure relieving means may be provided for relieving excessively high pressure which may build up in the prosthesis 10 under certain unusual circumstances, causing undesirable pressure to be exerted by prosthesis 10 on the organs and structures surrounding the chest cavity. Pressure may be exerted by balloon 12 on the surrounding structures when the patient, for example, enters a region of lower ambient atmospheric pressure, for example when the patient rides in an airplane or travels to high elevations.

The pressure relieving means may comprise, for example, a permeable panel in the subcutaneous infusion port which allows excess fluid to bleed into and be absorbed by the surrounding tissues, a pressure relief valve that vents excess fluid into a conduit which penetrates the patient's skin, or a normally empty reservoir bag 23 implanted subcutaneously and in communication with the balloon 12. In a preferred embodiment, referring to FIG. 1, reservoir bag 23 is normally empty since the mean pressure in balloon prosthesis 12 is generally below ambient atmospheric pressure. However, should the fluid inside balloon 12 expand for any reason, the excess volume will be displaced into reservoir bag 23.

Alternatively, in a fully grown patient, prosthesis 10 may be filled with a light liquid, such as liquid silicone, which would obviate the need for periodic volume adjustment and pressure relief means while maintaining the compliance of the prosthesis.

The balloon 12 and tube 14 of this prosthesis can be formed of any suitable biocompatible material, such as, for example, silicone materials, Mylar, and Dacron reinforced silicone material. A material should be chosen which evokes minimal fibrotic tissue response and pleural inflammation, and which is adequately inert to be suitable for long-term implantation. The rates at which the fluids interior and exterior to balloon 12 will pass through the chosen material, by osmosis or otherwise, should be taken into account when choosing the fluid or combination of fluids with which to fill balloon 12. In a preferred embodiment balloon 12 is constructed of silicone material, for example that used by CUI Corp., Carpenteria, Calif., with a wall thickness of, for example, approximately 0.5–1.5 mm. Filling tube 14 may be constructed of a like material with an interior diameter of 1.0 mm and a wall thickness of 0.5 mm. A suitable subcutaneous septal port 16 is commercially available from CUI Corp.

Contrary to the expectations of some practitioners, balloon prosthesis 10 of the present invention used experimentally in dogs have not experienced fluid influx and have remained gas-filled, although, as discussed above, gas transfer has been observed across the balloon membrane.

The balloon prosthesis 10 of this invention can be constructed to precisely fit into the chest cavity of a particular patient by a method for making balloon 12 comprising constructing a model of the patient's chest cavity using imaging means, building a mold for the balloon from the model, and manufacturing balloon 12 from the mold.

Figure 3:
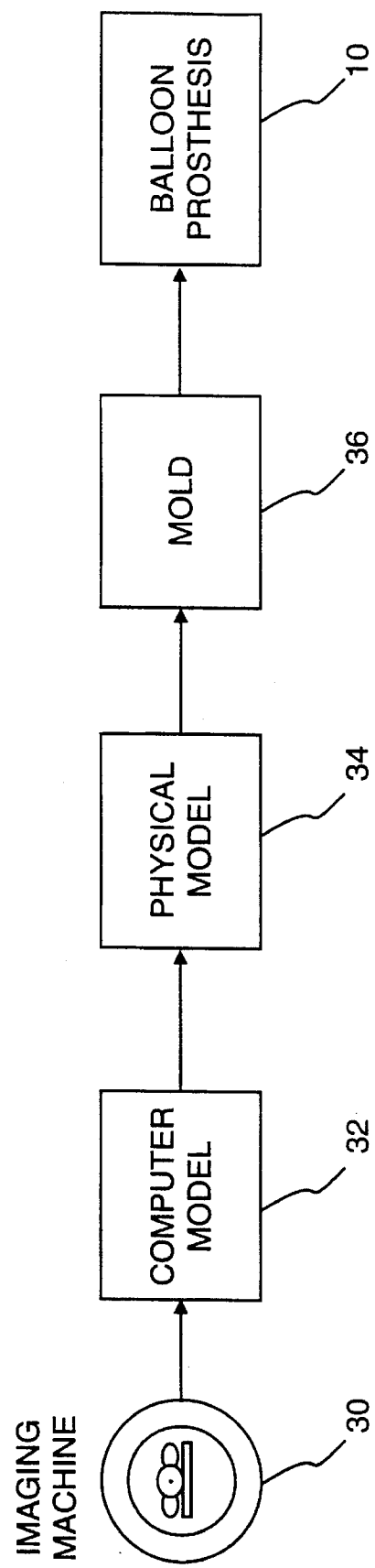
FIG. 3 is a block diagram of a method of making a customized prosthesis in accordance with this invention.

Referring to FIG. 3, in a preferred method of creating a customized prosthesis, computerized imaging means 30, which may be, for example, magnetic resonance imaging or computerized tomographic imaging, is utilized to generate a three-dimensional computer model 32 of the patient's chest cavity or of the lung which is to be replaced by the prosthesis. Computer model 32 may be obtained by the prosthesis fabricator from the hospital or clinic where the imaging is performed, or the fabricator may obtain the imaging data and generate computer model 32 itself. A physical model 34 of the chest cavity or lung may then be constructed from computer model 32 by conventional methods, for example using computerized machining equipment. Alternatively, the computer model 32 may be used to make a plurality of physical "slices" of the computer modeled shape, which slices may be fabricated and affixed together in proper alignment and orientation to produce a terraced physical model of the computer modeled shape. (The terraced surface of the model may then be smoothed by, for example, filling and cutting, to form physical model 34 of the patient's chest cavity.) Mold 36 may then be made from physical model 34 by conventional methods, and a custom fitted balloon 12 according to this invention may be constructed in mold 36 by molding methods well known in the art. Finally, filling tube 14, septal port 16 and other selected devices, for example pressure relieving means such as reservoir bag 23, may be attached to balloon 12 to form completed prosthesis 10.

In an alternative method, rather than customizing each prosthesis 12 to fit a particular patient, a plurality of prostheses over a range of suitable sizes and shapes may be constructed and made available to the physician in a kit, who may then select the appropriate prosthesis 12 from the kit for each patient who requires such a device.

FIGS. 4–7 demonstrate the gross anatomic distortions occurring after lung resection that are associated with significant fibrous adhesions. These adhesions lead to the kinking of blood vessels and airways that can result in clinical disability. Experimental evidence demonstrates that the nature of these distortions is similar in both man and dog. The unique geometry of the prosthesis helps preserve normal anatomy and function and prevents the development of rib cage collapse and fibrous adhesion of major thoracic structures as well as maintains patency of major blood vessels and airways.

Figure 4A:
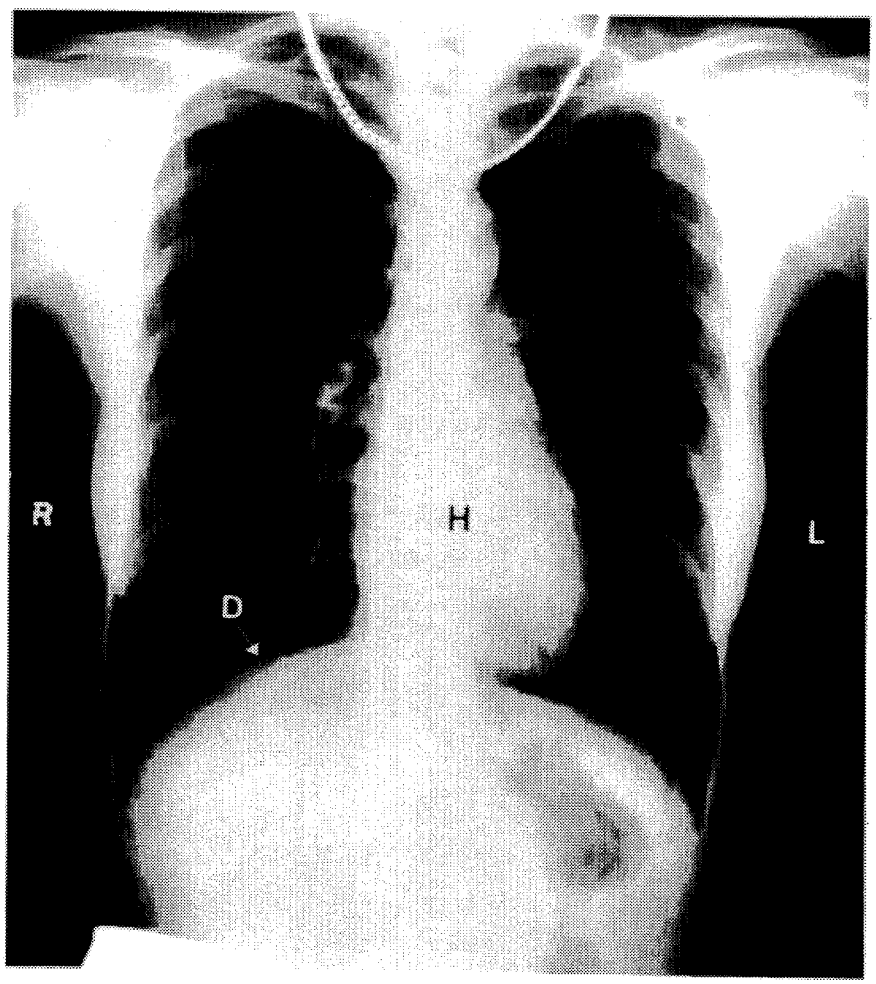
FIG. 4A is a chest x-ray from a normal human subject.

FIG. 4A is a chest x-ray from a normal human subject. The left (L) and right (R) sides are marked. The heart and major vessels (H) are surrounded by lung on both sides and are slightly left to the midline of the chest. The diaphragm (D), which separates the thorax from the abdomen, is normally dome shaped. The right half of the diaphragm is slightly higher than the left side.

Figure 4B:
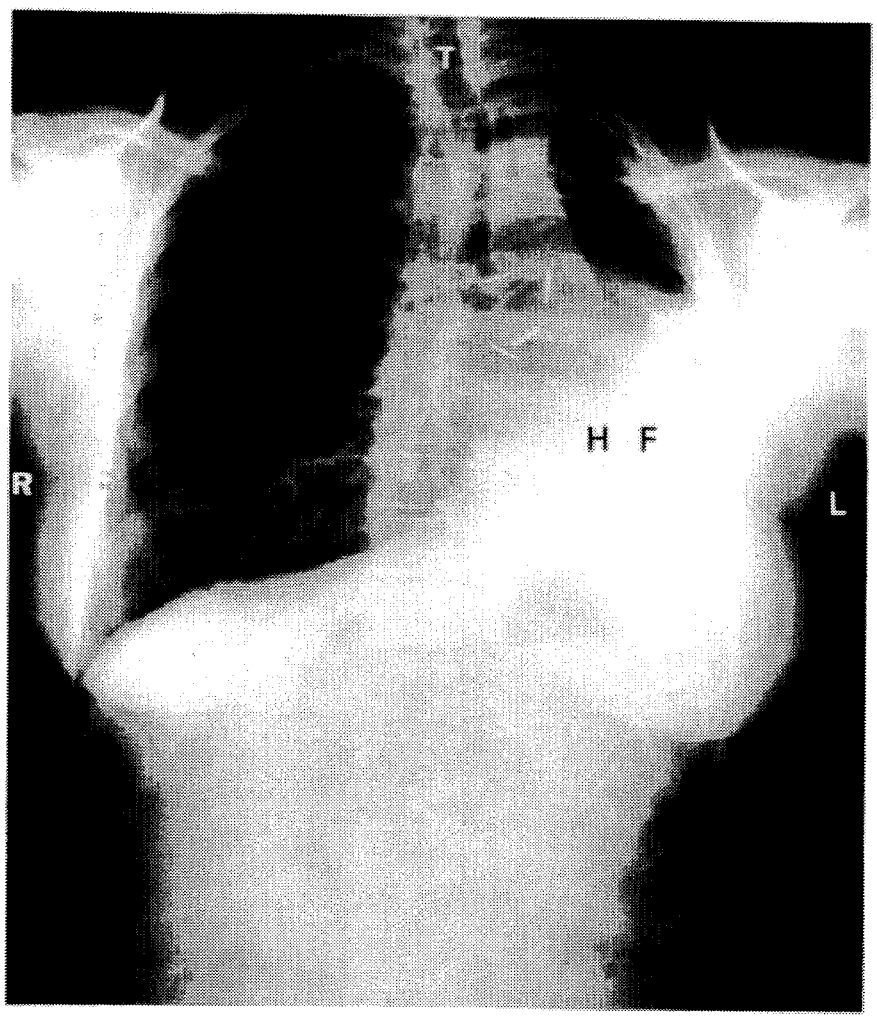
FIG. 4B is a chest x-ray from a human subject following pneumonectomy.

FIG. 4B is a chest x-ray from a patient after resection of the left lung. Without the support within the thorax that the left lung normally provides, the right lung hyperinflates, herniates across the midline into the left chest, and displaces the heart and major vessels (H) up against the left chest wall. Some degree of adhesion and fibrosis (F) is invariably present between the displaced heart and the inner surface of the chest wall, and cannot be separated from the heart shadow on regular x-ray. Also evident is that the tracheal air column (T) is also deviated to the left side. In some patients, this deviation may result in kinking of bronchi, resulting in respiratory distress.

Figure 5B:
FIG. 5B is a MRI image of the same patient following lung removal.
Figure 5A:
FIG. 5A is a magnetic resonance image (MRI) a human chest following pneumonectomy.

Referring to FIG. 5A, a magnetic resonance scan image of the chest in a patient whose right lung has been removed is demonstrated. Once again, the asymmetric shape of the chest is evident and the right rib cage has partially collapsed inward. The left ventricle of the heart (H) and large blood vessels are displaced into the right chest. A fibrous adhesion, which may restrict the normal motion and filling of the heart, is seen between the heart and the right rib cage, indicated by the dense white areas. The diaphragm (D) on the left side is of the normal dome shape but on the side of the lung resection, it is pulled up against the heart indicating further adhesion between the heart and the diaphragm.

FIG. 5B is another magnetic resonance image from the same patient after the right lung removal, from a different angle. In this figure, the aorta (A), which receives the entire output of the heart and is normally near the midline, is displaced into the right chest and against the rib cage. The vena cava (V), which returns all of the blood from the lower body to the heart and normally runs a straight course, is curved to the right. In some patients this curvature may lead to kinking of the vein, resulting in impaired blood flow.

Figure 6A:
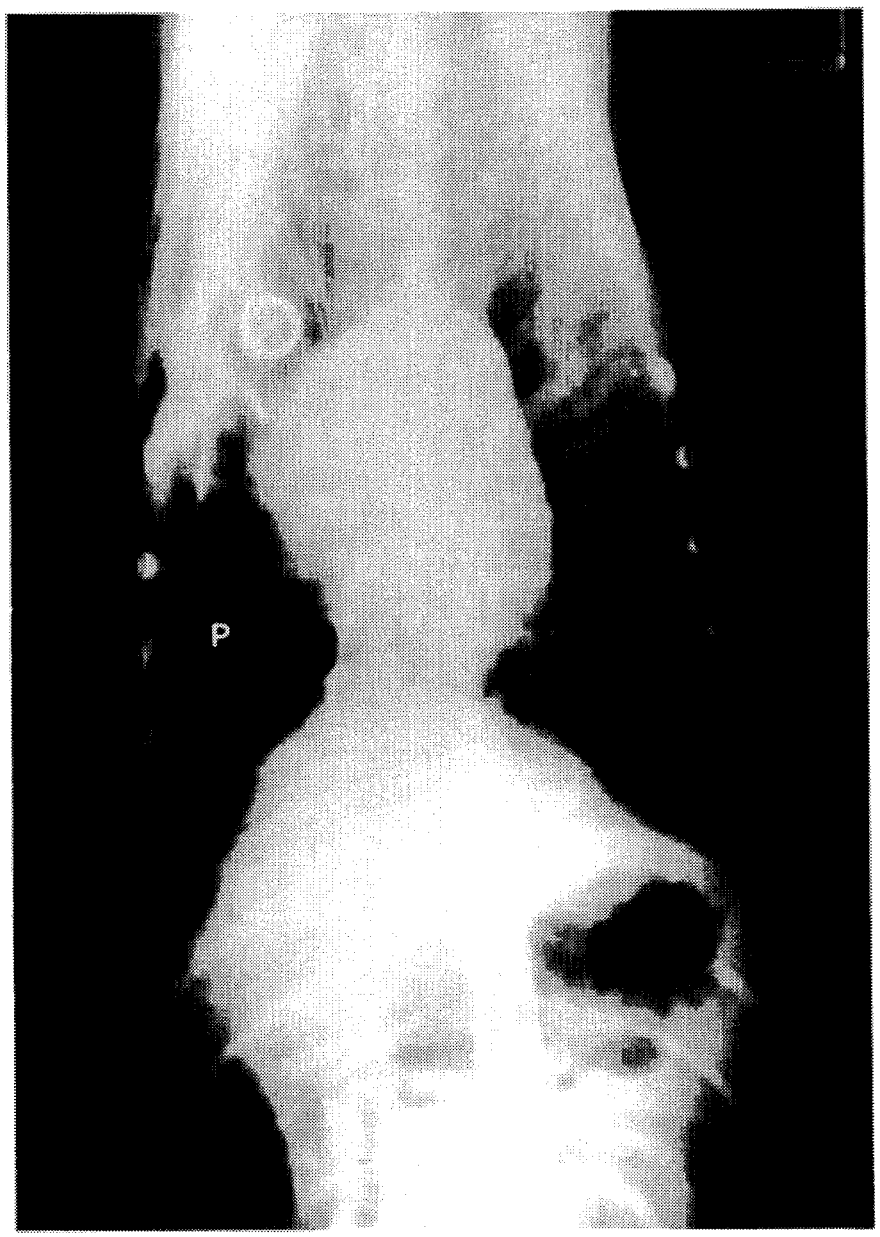
FIG. 6A demonstrates the implantation of a customized balloon prosthesis in a dog following right lung removal viewed by x-ray.

FIG. 6A is a chest x-ray from a dog after resection of the right lung and implantation of a customized balloon prosthesis (P) of the present invention in the right chest. The prosthesis has been partially inflated, and its folds are visible against the dark background of air. The dense ring shadow indicates the subcutaneous injection port. Because of the customized shape of the prosthesis, the "rib cage surface," lower "diaphragmatic surface" and "cardiac and mediastinal surface" are all in contact with the appropriate structures, supplying the necessary support to maintain the chest cavity in a manner similar to that prior to pneumonectomy. An important point to note is that the heart and major blood vessels are returned to the midline and are not adhering to the chest wall, and the diaphragm retains its normal dome shape.

Figure 6B:
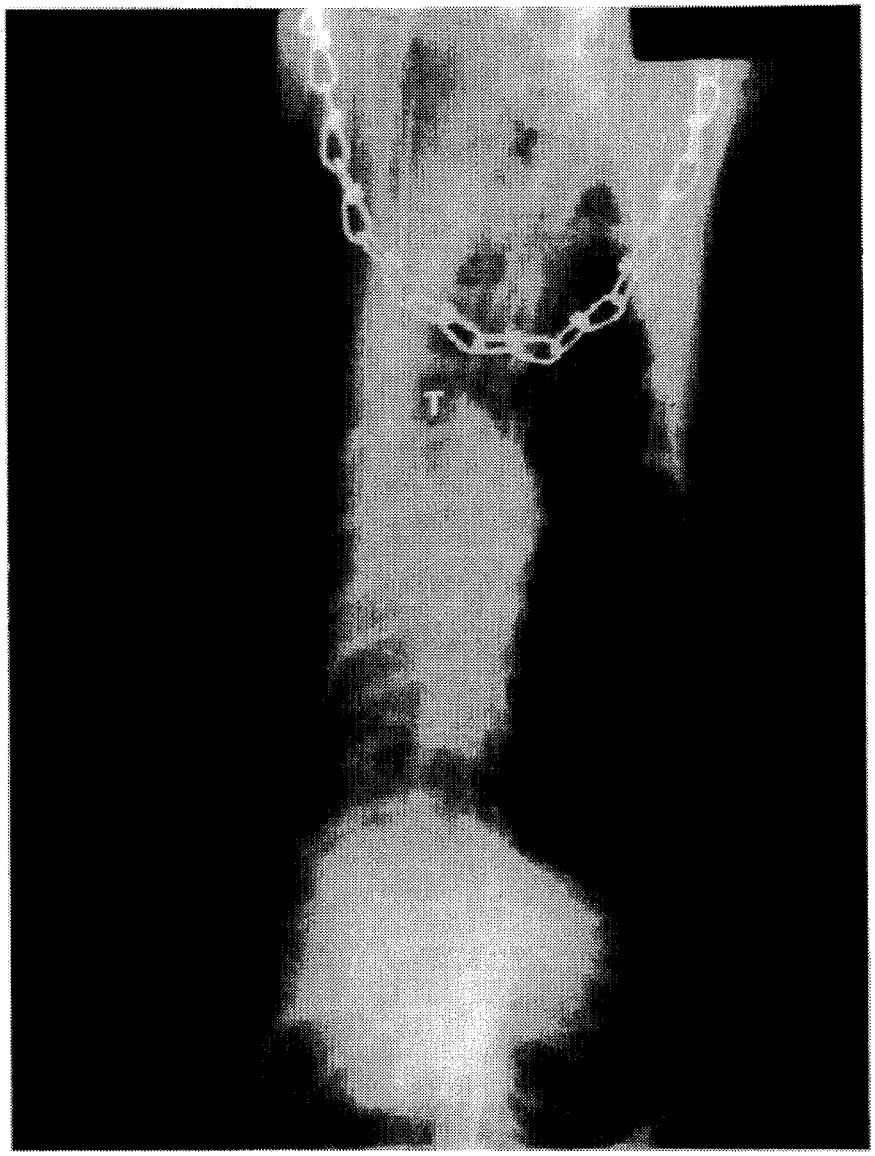
FIG. 6B shows an x-ray of a dog chest following resection of the right lung without implantation of a balloon prosthesis.

FIG. 6B is a chest x-ray of a dog following resection of the right lung, but without a prosthesis. It is clear that the heart shadow is displaced into the right chest and pressed against the rib cage, in a fashion similar to that seen in a human subject. Deviation of the tracheal air column (T) to the right is marked.

Figure 7A:
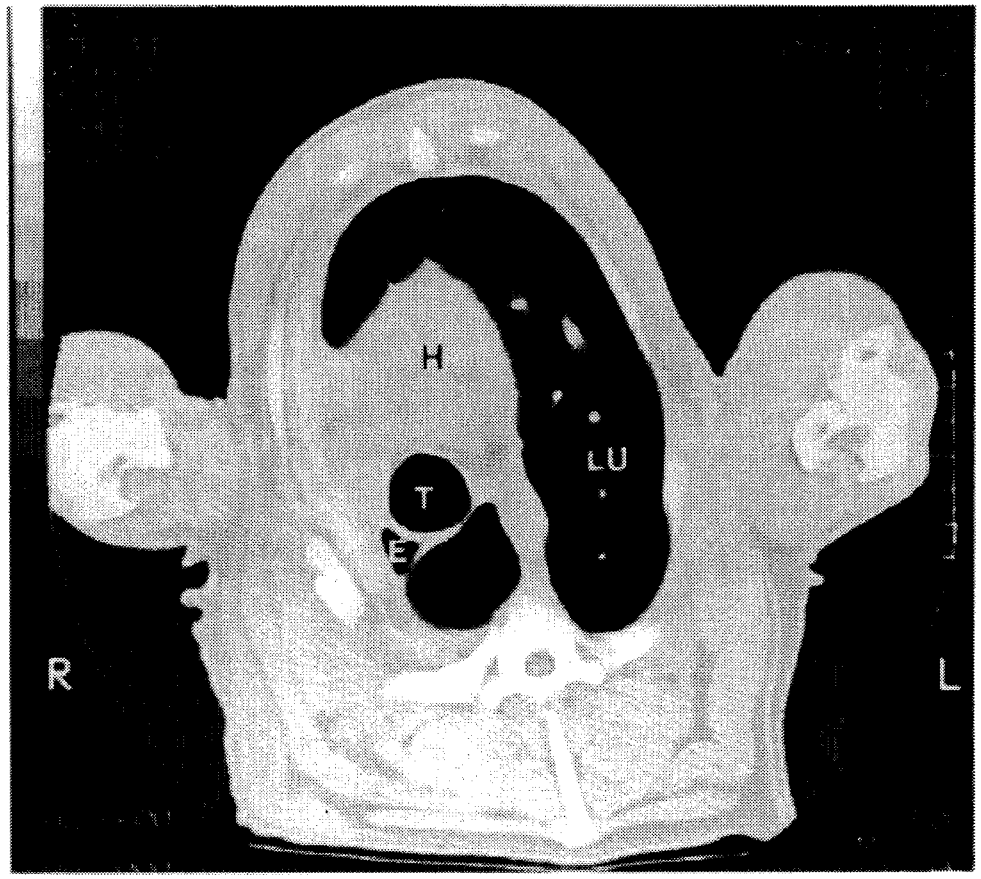
FIG. 7A shows a transverse image computerized tomographic (CT) scan of a dog chest following right lung removal.
Figure 7B:
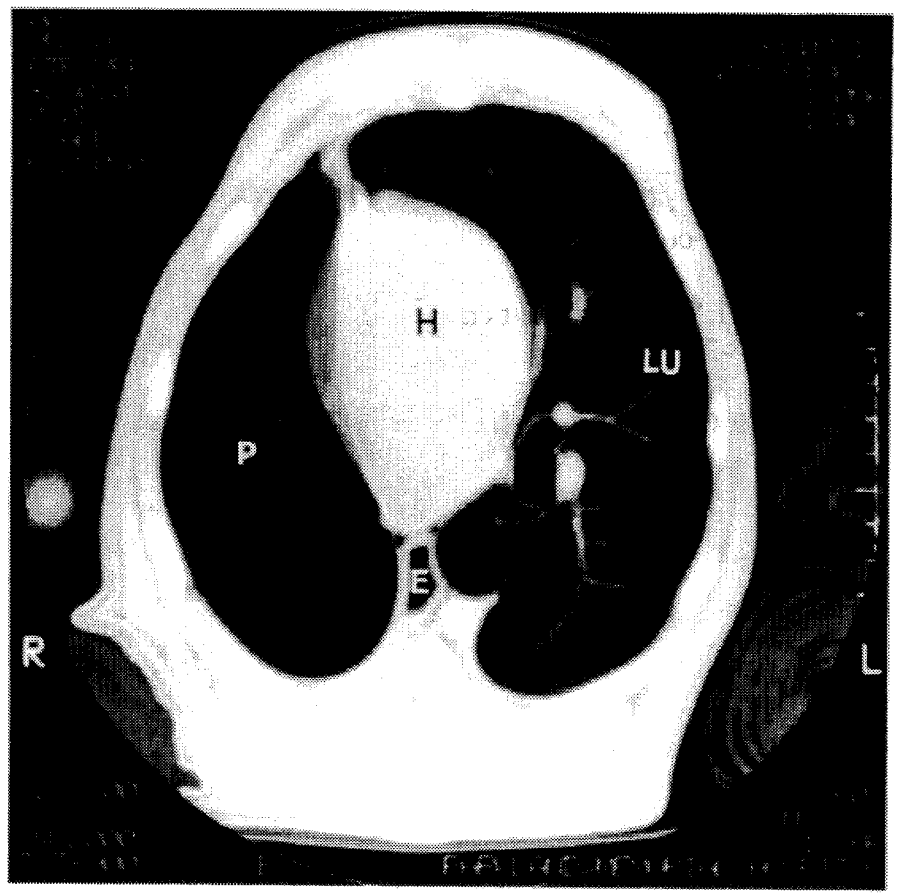
FIG. 7B demonstrates the implantation of the customized balloon prosthesis in a dog following right lung resection viewed by a transverse CT scan.

FIG. 7A is a high resolution computerized tomographic (CT) scan showing a transverse image from a dog after right lung resection without a prosthesis. Again, similar to the data from humans, the heart and major blood vessels (H) are deviated to the right side of the chest wall. Also markedly deviated to the right are the trachea (T) and esophagus (E). All of these structures are essentially pressed against the right rib cage, resulting in decreased function. The left lung (LU) herniates across the midline in front of the heart as well as behind the trachea and esophagus. Referring to FIG. 7B, the implantation of a customized, inflated balloon prosthesis (P) in a dog following right lung resection is demonstrated by a transverse CT scan. The heart and major blood vessels (H), as well as the esophagus (E) are returned to the midline and are free of adhesion to the rib cage. This image is taken at a lower level than FIG. 7A, so the trachea is not present in this image.

Thus, these images show that the customized balloon prosthesis of this invention is capable of maintaining or restoring the thoracic cavity to its original configuration following pneumonectomy, allowing the remaining organs to function without physical impairment that occurs by shifting into the unoccupied space left by the missing lung. Other known prostheses are either cosmetic, as in the case of breast implants, or functional in a manner not related to structure, such as bladder implants or tissue expanders. Only the novel and custom designed prosthesis supplied by this invention is able to restore normal thoracic cavity organ position following removal of a lung or part thereof.

The inventions disclosed herein are intended for human use as well as for veterinary use.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size, and arrangement of parts. For example, equivalent elements or materials may be substituted for those illustrated and described herein, and certain features of the invention may be utilized independently of the use of other features, all as would be apparent to one skilled in the art after having the benefit of this description of the invention.

What is claimed is:

1. A prothesis having a predetermined shape and size to occupy a chest cavity left vacant after excision of a lung or portion of a lung, comprising:

a hollow balloon forming an enclosed volume adapted to occupy the chest, and formed in substantially the shape and size of the chest cavity, the balloon having a first surface corresponding in shape to the contour chest cavity adjacent to the rib cage a second surface corresponding in shape to the contour of the chest cavity adjacent to the diaphragm, and a third surface corresponding in shape the contour of cardiac and mediastinal surface of the chest wall, the balloon being made of a biocompatible material.

2. The prosthesis of claim 1, further comprising a filling tube made of a biocompatible material having a first end and a second end, the first end being connected to the balloon.

3. The prosthesis of claim 2, further comprising a subcutaneous septal port connected to the second end of the filling tube, the port having a self-sealing surface adapted to be penetrated by a hypodermic needle.

4. The prosthesis of claim 1, further comprising:

a gaseous mixture comprising an inert gas occupying the enclosed volume formed by the balloon.

5. The prosthesis of claim 4, wherein the inert gas comprises sulfur hexafluoride.

6. The prosthesis of claim 1, further comprising:

a liquid solution comprising silicone occupying the enclosed volume formed by the balloon.

7. The prosthesis of claim 1, wherein the balloon is constructed from silicone material.

8. The prosthesis of claim 1, wherein the balloon is a selected amount larger in size than the chest cavity it is intended to occupy.

9. The prosthesis of claim 2, wherein a subcutaneous septal port is connected to the second end of the filling tube, the port having a self-sealing surface adapted to be penetrated by a hypodermic needle.

10. The prosthesis of claim 2, further comprising:

a pressure relieving means adapted to permit fluid to exit the balloon to prevent the balloon from exerting excessive pressure upon surrounding organs when the fluid in the balloon expands.

11. The prosthesis of claim 10, wherein the pressure relieving means comprises a subcutaneous reservoir bag adapted to accept fluid from the balloon.

12. The prosthesis of claim 10, wherein the pressure relieving means comprises a permeable panel located on the subcutaneous septal port adapted to permit fluid to exit the prosthesis and be absorbed into surrounding tissue.

13. The prosthesis of claim 10, further comprising:

a gaseous mixture comprising an inert gas occupying the enclosed volume formed by the balloon.

14. The prosthesis of claim 13, wherein the inert gas comprises sulfur hexafluoride.

15. The prosthesis of claim 10, further comprising:

a liquid solution comprising silicone occupying the enclosed volume formed by the balloon.

16. The prosthesis of claim 10, wherein the balloon is constructed from silicone material.

17. The prosthesis of claim 10, wherein the balloon is a selected amount larger than the chest cavity it is intended to occupy.

18. A method for preventing mediastinal shift and overdistension and displacement of organs following pneumonectomy, comprising:

providing a prosthesis comprising a hollow balloon formed in substantially the shape and size of the lung it is intended to replace, the balloon having a first surface corresponding to the chest cavity adjacent to the rib cage, a second surface corresponding to the contour of the chest cavity adjacent to the diaphragm, and a third surface corresponding to the contour of the cardiac and mediastinal surface of the chest wall, the balloon being manufactured from a biocompatible material, a filling tube manufactured from a biocompatible material having a first end and a second end, the first end being connected to the balloon, and a subcutaneous septal port connected to the second end of the filling tube, the port having a self-sealing surface adapted to be penetrated by a hypodermic needle;

surgically implanting the balloon of the prosthesis in a vacant chest cavity;

positioning the filling tube leading from the balloon to a site selected for implanting the subcutaneous septal port;

implanting the subcutaneous septal port at the selected site; and filling the balloon to a selected volume with fluid; wherein said prosthesis prevent mediastainal shift and overdistension and displacement of organs following pnuemonectomy.

19. The method of claim 18, further comprising adjusting the volume of the balloon by penetrating the self-sealing surface of the subcutaneous septal port with a hypodermic needle and adding fluid to or removing fluid from the prosthesis.

20. A method of making a balloon prosthesis for a lung, comprising:

obtaining a computer model of the chest cavity;

forming a physical model of the chest cavity from the computer model;

constructing a mold from the physical model; and molding a hollow balloon in the mold using a biocompatible material, such that the balloon is substantially the size and shape of the chest cavity, the balloon having a rib cage surface, a diaphragmatic surface, and a cardiac and mediastinal surface.

21. A kit for use by physicians, said kit comprising a plurality of balloon prostheses from which a physician can select a balloon prosthesis of a size and shape suitable to occupy a chest cavity having a determinable size and shape vacated after a lung is excised from a patient, said prostheses being made of biocompatible materials and formed in substantially the sizes and shapes of the chest cavities they are intended to occupy, and said prostheses each having a first surface corresponding in shape to the contour chest cavity adjacent to the rib cage, a second surface corresponding in shape to the contour of the chest cavity adjacent to the diaphragm, and a third surface corresponding in shape to the contour of the cardial and mediastinal surface of the chest wall.

22. A method for preventing mediastinal shift and overdistension and displacement of organs following pneumonectomy, comprising:

providing a prosthesis comprising a hollow balloon formed in substantially the shape and size of the lung it is intended to replace, the balloon having a surface corresponding to the chest cavity adjacent to the rib cage, a surface corresponding to the contour of the chest cavity adjacent to the diaphragm, and a surface corresponding to the contour of the cardiac and mediastinal surface of the chest wall, the balloon being manufactured from a biocompatible material; and surgically implanting the balloon in a vacant chest cavity wherein; said prosthesis prevents mediastinal shift and overdistension and displacement of organs following pnuemonectomy.

23. A method for preventing mediastinal shift and overdistension and displacement of organs following pneumonectomy, comprising:

providing a prosthesis comprising a hollow balloon formed in substantially the shape and size of the lung it is intended to replace, the balloon having a surface corresponding to the chest cavity adjacent to the rib cage, a surface corresponding to the contour of the chest cavity adjacent to the diaphragm, and a surface corresponding to the contour of the cardiac and mediastinal surface of the chest wall, the balloon being manufactured from a biocompatible material and filled with fluid, a filling tube manufactured from a biocompatible material having a first end and a second end, the first end being connected to the balloon, and a subcutaneous septal port connected to the second end of the filling tube, the port having a self-sealing surface adapted to be penetrated by a hypodermic needle;

surgically implanting the balloon of the prosthesis in a vacant chest cavity;

positioning the filling tube leading from the balloon to a site selected for implanting the subcutaneous septal port;

implanting the subcutaneous septal port at the selected site; and filling the balloon to a selected volume with fluid; wherein said prosthesis prevents mediastinal shift and overdistension and displacement of organs following pnuemonectomy.

24. The method of claim 23, further comprising adjusting the volume of the balloon by penetrating the self-sealing surface of the subcutaneous septal port with a hypodermic needle and adding fluid to or removing fluid from the prosthesis.

25. A prosthesis having a predetermined shape and size to occupy a chest cavity left vacant after excision of a lung or portion of a lung, comprising:

a hollow balloon forming an enclosed volume adapted to occupy the chest, and formed in substantially the shape and size of the chest cavity, the balloon having a first surface corresponding to the chest cavity adjacent to the rib cage, a second surface corresponding to the contour of the chest cavity adjacent to the diaphragm, and a third surface corresponding to the contour of the cardiac and mediastinal surface of the chest wall, the balloon being made of a biocompatible material;

a filling tube made of a biocompatible material having a first end and a second end, the first end being connected to the balloon;

a subcutaneous septal port connected to the second end of the filling tube, the port having a self-sealing surface adapted to be penetrated by hypodermic needle;

a pressure relieving means adapted to permit fluid to exit the balloon to prevent the balloon from exerting excessive pressure upon surrounding organs when the fluid in the balloon expands; and wherein the pressure relieving means comprises a permeable panel located on the subcutaneous septal port adapted to permit fluid to exit the prosthesis and be absorbed into surrounding tissue.

* * * * *

UNITED STATES PATENT AND TRADEMARK OFFICE
CERTIFICATE OF CORRECTION

PATENT NO.   :   5,578,085

DATED        :   November 26, 1996

INVENTOR(S)  :   Robert L. Johnson, Jr.; Connie C. W. Hsia,

It is certified that error appears in the above-identified patent and that said Letters Patent is hereby corrected as shown below:

In claim 1, column 9, line 43, delete "shape the" and insert --shape to the-- therefor.

Signed and Sealed this

Twenty-fifth Day of March, 1997

*Attest:*

BRUCE LEHMAN

*Attesting Officer*   Commissioner of Patents and Trademarks